United States Patent [19]
Reiser

[11] Patent Number: 5,976,124
[45] Date of Patent: Nov. 2, 1999

[54] PHOTOTHERAPY DEVICE AND METHOD

[75] Inventor: Christopher Reiser, Colorado Springs, Colo.

[73] Assignee: Spectranetics Corporation, Colorado Springs, Colo.

[21] Appl. No.: 09/002,869

[22] Filed: Jan. 5, 1998

[51] Int. Cl.⁶ .................................................. A61B 17/36
[52] U.S. Cl. ................................................. 606/14; 606/15
[58] Field of Search ................................... 606/1, 13, 14, 606/15, 16, 17, 7, 8, 9, 10, 11, 12

[56] References Cited

U.S. PATENT DOCUMENTS

| | | |
|---|---|---|
| 4,658,817 | 4/1987 | Hardy . |
| 4,799,479 | 1/1989 | Spears . |
| 4,852,567 | 8/1989 | Sinofsky . |
| 4,881,524 | 11/1989 | Boebel . |
| 5,063,280 | 11/1991 | Inagawa . |
| 5,125,926 | 6/1992 | Rudko . |
| 5,156,604 | 10/1992 | Hessel et al. ............................. 606/15 |
| 5,172,699 | 12/1992 | Svenson . |
| 5,190,538 | 3/1993 | Hussein . |
| 5,200,604 | 4/1993 | Rudko . |
| 5,290,276 | 3/1994 | Sewell, Jr. ............................... 606/15 |
| 5,298,026 | 3/1994 | Chang .................................... 606/15 |
| 5,380,316 | 1/1995 | Aita . |
| 5,389,096 | 2/1995 | Aita . |
| 5,454,782 | 10/1995 | Perkins ................................... 606/15 |
| 5,469,524 | 11/1995 | Esch et al. .............................. 606/15 |
| 5,549,601 | 8/1996 | McIntyre et al. ....................... 606/15 |
| 5,554,152 | 9/1996 | Aita . |
| 5,591,159 | 1/1997 | Taheri ..................................... 606/15 |
| 5,591,161 | 1/1997 | Negus . |
| 5,607,421 | 3/1997 | Jeevanandam . |
| 5,607,606 | 3/1997 | Mori . |
| 5,617,258 | 4/1997 | Negus . |
| 5,855,577 | 1/1999 | Murphy-Chittorian et al. ........ 606/15 |

Primary Examiner—Linda C. M. Dvorak
Assistant Examiner—Sonya Harris-Ogugua
Attorney, Agent, or Firm—Pillsbury Madison & Sutro, LLP

[57] ABSTRACT

A phototherapy device has a phototherapy handpiece, an optical fiber attached to the phototherapy handpiece, and a laser phototherapy light source. The phototherapy handpiece, has a handpiece body that defines an interior region and has an outer surface which defines a foot of the phototherapy handpiece, an optical fiber drive assembly disposed at least partially within the interior region of the handpiece body has an optical fiber attachment portion that is movable relative to the handpiece body. The optical fiber drive assembly includes a driving component which causes the attachment portion to move relative to the handpiece body, and a damping component which resists the motion of the optical fiber attachment portion such that the optical fiber attachment portion attains a substantially constant speed motion relative to the handpiece body.

20 Claims, 3 Drawing Sheets

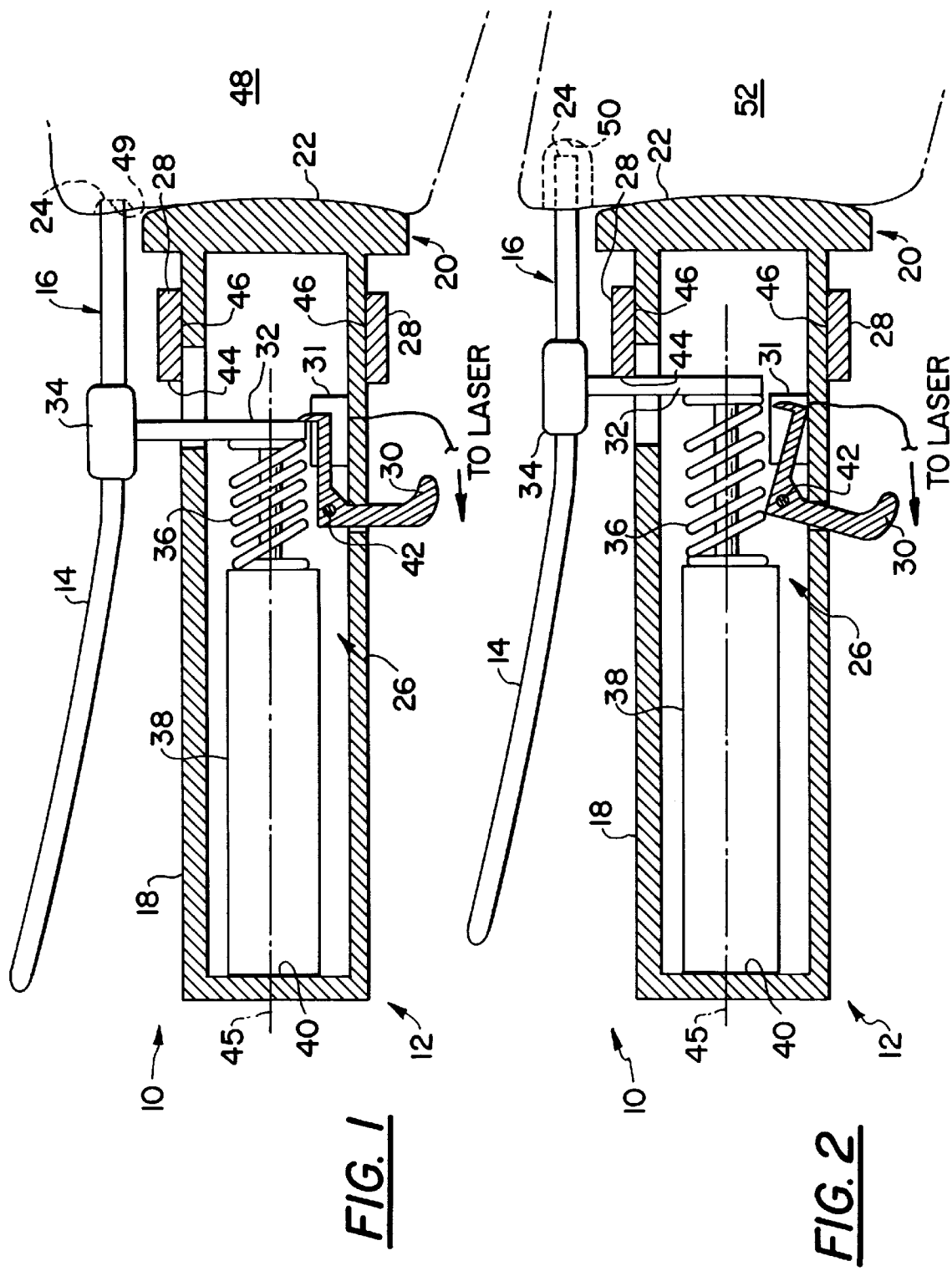

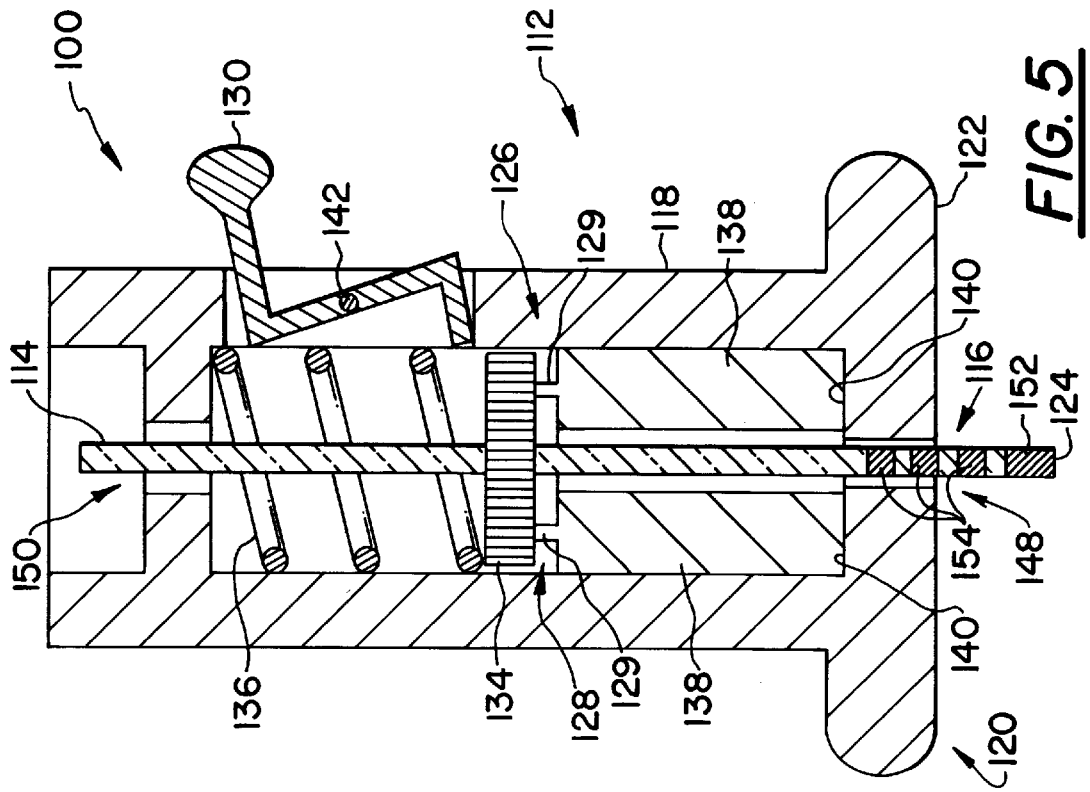
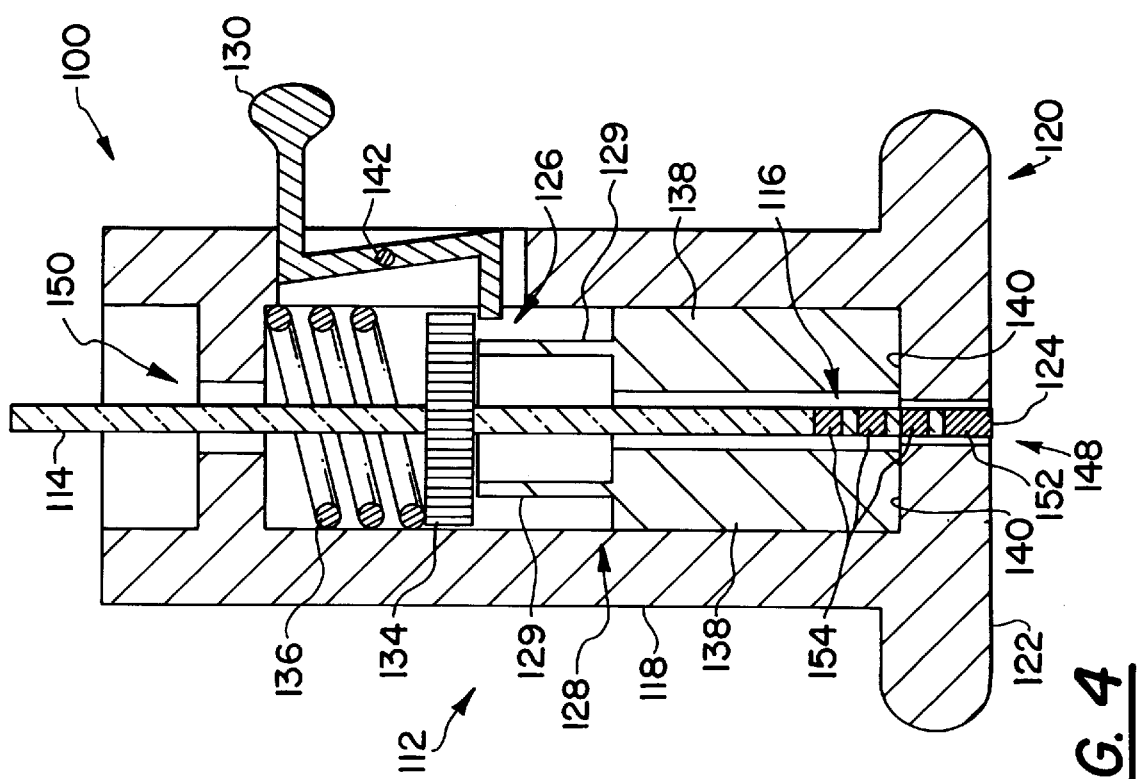

PHOTOTHERAPY DEVICE AND METHOD

BACKGROUND OF THE INVENTION

1. Field of the Invention

The present invention pertains to a phototherapy device and method, and more particularly to a handpiece and method for advancing an optical fiber.

2. Description of the Related Art

Devices and methods for performing various types of laser surgery using optical fibers have become widespread. One relatively new application is myocardial revascularization which is used as an alternative to coronary artery bypass surgery. Trans-myocardial revascularization is a method for treating ischemic heart disease in which the heart muscle or myocardium does not receive an adequate blood supply. Trans-myocardial revascularization helps supplement the blood supply delivered to the heart by providing the heart muscle with direct access to blood within the ventricle chamber.

Lasers have been proposed in trans-myocardial laser revascularization to produce channels in the ventricle wall. The channels provide blood flow to the ischemic heart muscle. Optical fibers are useful for directing laser energy to the desired regions of the heart muscle. However, in order for lasers to be effective in trans-myocardial revascularization, the energy from the laser must be concentrated on a narrow region of the heart tissue. As tissue is ablated, if the optical fiber is held in a fixed position, the surface being cut moves away from the area of greatest laser energy concentration. Consequently, optical fibers are advanced in the cutting direction as the tissue is ablated in order to concentrate energy on the heart tissue. In other words, one may think of the optical fiber as ablating a channel through the heart tissue. If the laser energy is not concentrated on a sufficiently narrow region of the heart tissue, the laser begins to heat up regions of the heart tissue without ablating narrow regions of tissue. This can lead to blood coagulation and damage to the heart tissue.

Devices are known in the art for advancing optical fibers using electric motors. However, such devices are complicated and expensive.

Mechanical devices are also known in which optical fibers are advanced manually by the operator through a rack-and-pinion type of mechanism. However, such devices have the disadvantage that it is difficult to control the speed of the forward advancement since the speed depends on the operator moving a lever or some similar mechanical device.

SUMMARY OF THE INVENTION

Accordingly, it is an object of this invention to provide a mechanical device which advances an optical fiber in a phototherapy device at a substantially constant rate of speed.

It is another object of this invention to provide a phototherapy device which provides the operator with good control over the advancement of an optical fiber.

It is another object of this invention to provide a trans-myocardial laser revascularization device in which an optical fiber is advanced at substantially a constant rate of speed by a mechanical device which is easily controllable by the operator.

It is a further object of this invention to provide a trans-myocardial laser revascularization method.

The above and related objects of this invention are realized by providing a phototherapy handpiece having a drive assembly which mechanically advances an optical fiber attached to the phototherapy handpiece in the direction of the emitted radiation, at substantially a constant speed.

The drive assembly has a driving component, preferably a spring, which forces the optical fiber in the direction of the emitted radiation. However, since driving components such as springs alone do not generate a constant forward motion to an object attached to an end of the spring, the drive assembly also has a damping component that resists the motion produced by the driving component. Preferably, the damping component is a hydraulic cylinder. Such hydraulic cylinders produce a resisting force which increases with increasing speed. Consequently, the combination of the driving spring and the damping hydraulic cylinder yields a substantially constant speed advancement of the optical fiber in the direction of the emitted radiation.

The phototherapy handpiece preferably has a catch mechanism which holds the optical fiber in a retracted position. The operator of the phototherapy handpiece can release the catch mechanism at a desired moment. Upon releasing the catch mechanism, the driving component (the spring in the preferred embodiment) forces the optical fiber in the direction of the emitted radiation from the end of the optical fiber. The optical fiber advances at a substantially constant rate of speed due to the resistance of the damping component.

In the preferred embodiment, a mechanical limiter is set at a selectable position to stop the forward motion of the optical fiber at a preselected point. The mechanical limiter can be an annular ring which is attached to the outer surface of the phototherapy handpiece in the preferred embodiment. Preferably, the phototherapy handpiece is cylindrical and the mechanical limiter is attached to it by threads. The mechanical limiter can then be rotated to adjust its position.

The laser phototherapy light source is preferably turned on by the action of the catch mechanism as the operator releases the catch such that the optical fiber can move in the direction of radiation being emitted.

The invention also encompasses a trans-myocardial laser revascularization method. According to the trans-myocardial laser revascularization method of this invention, the operator performs work on a phototherapy handpiece, such as by compressing a spring which serves as the drive component in the preferred embodiment. This step can be thought of as loading the phototherapy handpiece. The operator places a distal portion of the phototherapy handpiece in contact with a region of the patient's body. The operator then releases the catch mechanism on the optical fiber drive assembly which permits the optical fiber to move at a substantially constant speed in the direction of the emitted radiation.

These and other objects and advantages of the present invention will be apparent from the detailed description, the accompanying drawings, and the claims.

BRIEF DESCRIPTION OF THE DRAWINGS

FIG. 1 is a cross-sectional view of the trans-myocardial laser revascularization device according to a first preferred embodiment of the invention, with the catch mechanism holding the drive assembly in the loaded position;

FIG. 2 is a cross-sectional view of the trans-myocardial laser revascularization device according to the first preferred embodiment of the invention in which the catch mechanism is in a released position;

FIG. 4 is a cross-sectional view of a second preferred embodiment of the trans-myocardial laser revascularization device in a loaded position; and FIG. 5 is a cross-sectional view of the trans-myocardial laser revascularization device according to the second preferred embodiment of the invention with the catch mechanism in a released position.

DETAILED DESCRIPTION OF THE PREFERRED EMBODIMENT

Figure 3:
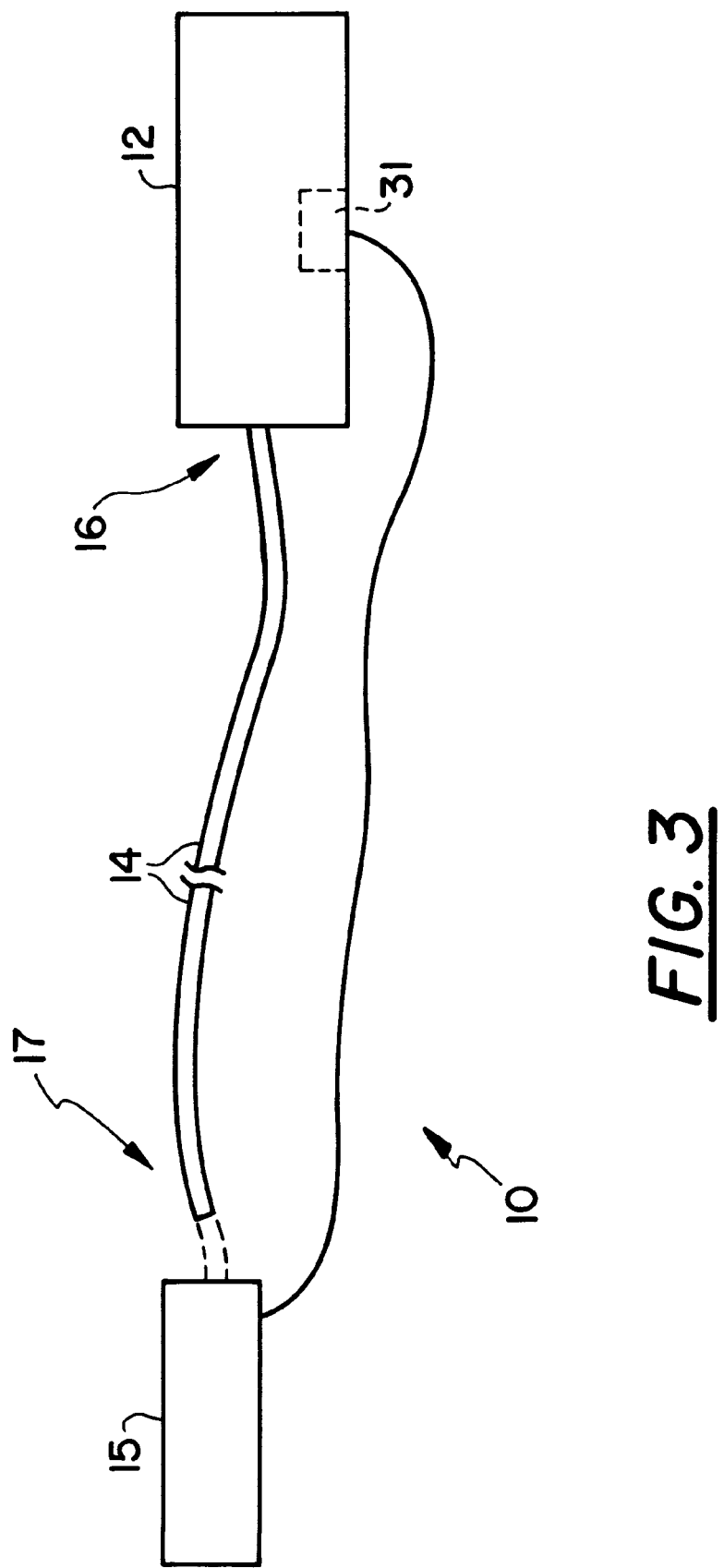
FIG. 3 is a schematic illustration of the laser revascularization device according to the first preferred embodiment of the invention.

The trans-myocardial laser revascularization device according to the present invention is designated generally by the reference numeral 10 in FIGS. 1 and 2. The trans-myocardial laser revascularization device 10 has a phototherapy handpiece 12, an optical fiber 14 attached to the phototherapy handpiece 12, and a laser phototherapy light source 15 (see FIG. 3). The optical fiber 14 is attached to the phototherapy handpiece 12 near the distal end 16 of the optical fiber. The proximal end 17 of the optical fiber 14, shown in FIG. 3, is attached to a laser phototherapy light source 15 such that light from the laser is directed into the optical fiber (see FIG. 3). Suitable phototherapy light sources are excimer lasers such as xenon-chloride lasers, or holmium-yttrium-aluminum garnet (Ho:YAG) lasers. The optical fiber 14 may be a single fiber, or a fiber bundle. The term "optical fiber" is used in its general sense in this invention to encompass both a single fiber and a fiber bundle.

As one may best view in FIGS. 1 and 2, the phototherapy handpiece 12 has a handpiece body 18 which defines an interior region. The handpiece body 18 has a portion known as a foot 20. The foot 20 has an outer surface 22 with a much greater surface area than the light emitting end 24 of the optical fiber 14. The large surface area of the outer surface 22 of the foot 20 permits the reduction of applied pressure when the surface 22 of the phototherapy handpiece 12 is brought into contact with portions of the patient's body. A suitable material for the handpiece body 18 is polycarbonate or stainless steel.

The phototherapy handpiece 12 also has a drive assembly 26, a mechanical limiter 28 and a catch mechanism 30. For the first preferred embodiment, the drive assembly 26 has a connecting member 32 attached to an optical fiber attachment portion 34. The connecting member 32 is forced in a distal direction by a driving component 36. In a preferred embodiment, the driving component 36 is a spring which the operator compresses to store energy as potential energy from the work done on the spring while compressing it. However, the invention is not limited to having a spring as the driving component 36. One skilled in the art would recognize that there are numerous embodiments in which one may select a driving component which stores work done as potential energy which in turn can be reconverted back into kinetic energy. Such alternate driving components include, but are not limited to, compressed air cylinders, gravimetric weights, or electromechanical solenoids. The drive assembly 26 also has a damping component 38. In the first preferred embodiment, the damping component 38 has an end 40 with a fixed position relative to the handpiece body 18. The end 40 of the damping component 38 defines a region of contact between the drive assembly 26 and the handpiece body 18 such that the end 40 of the damping component 38 remains substantially fixed relative to the handpiece body 18 as the connecting member 32 and optical fiber connecting portion 34 move.

The damping component 38 supplies a damping force on the connecting member 32 and optical fiber connecting portion 34 with a strength that depends on the speed of the connecting member 32 and directed so as to oppose the motion of the connecting member 32 and optical connecting portion 34. In the preferred embodiment, the damping component 38 is a hydraulic cylinder. However, other types of damping components may be used for the damping component 38 without departing from the scope and spirit of the invention. Such alternative damping components include, but are not limited to air-damped dashpots or turbines.

The catch mechanism 30 is similar to a trigger mechanism and it is pivotally attached at a point 42 in the first preferred embodiment. The catch mechanism 30 has a first position, as one may see illustrated in FIG. 1, which holds the drive assembly in a higher potential energy state, for example, so that spring 36 is compressed. FIG. 2 shows a second position of the catch mechanism 30 in which the catch mechanism 30 is rotated about the pivot point 42. In the second position of the catch mechanism 30 the connecting member 32 and optical fiber attachment portion 34 are free to move without being constrained by the catch mechanism 30. Although the preferred embodiment uses a catch mechanism 30 with a trigger-like structure, other catch mechanisms may be used without departing from the scope and spirit of the invention. Such alternative structures include, but are not limited to, magnetic latches, solenoids, or springloaded detent mechanisms.

If one uses a solenoid catch release instead of the trigger-like catch mechanism 30 of the preferred embodiment, the light source 15 may transmit a signal to activate the solenoid which releases the catch. One may obtain coordination of fiber motion with light emission by causing the signal to coincide with the onset of light emission.

The mechanical limiter 28 is preferably adjustable to set an end 44 of the mechanical limiter 28 to a selectable position. In the first preferred embodiment, the mechanical limiter 28 is connected to the handpiece body 18 by conventional threading 46.

The catch mechanism 30 includes a switch 31, which turns the laser phototherapy light source 15 on when the catch mechanism 30 is changed from the first to the second position.

In operation, the user adjusts the mechanical limiter 28 such that the mechanical limiter end 44 is at a desired position to stop the progression of the optical fiber 14 such that the light emitting end 24 of the optical fiber 14 will be at a pre-selected position relative to the surface 22 of the foot 20. In a preferred embodiment, the mechanical limiter 28 is adjusted by rotating it about an axis 45. The operator performs work on the driving component 36 to store potential energy in the driving component 36. In the preferred embodiment, this is done by compressing the spring 36. The driving component 36 is held in the higher potential energy state by the catch mechanism 30, which one may consider as being a "loaded" position.

The operator of the trans-myocardial laser revascularization device 10 places the surface 22 of the foot 20 in contact with a selectable portion of the patient's body, for example, with a selectable portion of the patient's heart. The large area of the surface 22 helps spread the applied force over a greater area, thus decreasing the applied pressure. This helps prevent tissue damage. When the trans-myocardial laser revascularization device 10 is in position, the operator selects a desired time to initiate phototherapy by pulling the trigger-like catch mechanism 30. By pulling the catch mechanism 30 such that the catch mechanism 30 moves from the first position to the second position, the laser phototherapy light source 15 turns on and the optical fiber 14 becomes free to move under the influence of the driving assembly 26 such that the light emitting surface 24 moves in the direction of the light emission as time progresses.

The force of the spring 36 is opposed by the hydraulic cylinder 38 to produce a substantially constant speed progression of the light emitting surface 24 in the direction of the emission of light. The desired speed of progression of the light-emitting surface 24 of the optical fiber 14 can be selected by selecting appropriate combinations of driving components 36 and damping components 38. For example, one may select springs having various spring constants and hydraulic cylinders with various damping characteristics.

After the operator pulls the trigger-like catch mechanism 30, the optical fiber 14 then moves at a substantially constant speed until it reaches the mechanical limiter 28. The progression of the optical fiber 14 is then stopped by the mechanical limiter 28.

FIGS. 1 and 2 provide schematic illustrations of the surgical effect produced by the trans-myocardial laser revascularization device according to this invention. In FIG. 1, the surgical region of the patient is represented generally by reference numeral 48 at a time before the catch mechanism 30 has been released. FIG. 1 illustrates the light-emitting end 24 of the optical fiber 14 at a time it is pressed into the region 49 before it has cut into the surgical region of the patient 48. As laser energy is emitted from the light-emitting surface 24 of the optical fiber 14, it cuts into the surgical region of the patient 52, as is illustrated in FIG. 2. The surgical energy from the laser is more efficiently and accurately deposited at a specific region by maintaining the light-emitting surface 24 close to the incision point 50 of the surgical region 52 at a time after releasing the catch mechanism 30. If the incision point 50 is allowed to be cut back too far without advancing the optical fiber 14 in the direction of the emitted laser energy, the energy becomes too disperse to cut the tissue and begins to heat and damage the tissue.

A second preferred embodiment of the invention is illustrated in FIGS. 4 and 5, and generally represented by reference numeral 100. The trans-myocardial laser revascularization device 100 according to the second preferred embodiment has a photo-therapy handpiece 112, an optical fiber 114, and a laser photo-therapy light source (not shown in FIGS. 4 and 5). The optical fiber 114 may be a single fiber, or a fiber bundle. The optical fiber 114 has a distal end 116.

The photo-therapy handpiece 112 has a handpiece body 118 which defines a foot 120 having a surface 122. The surface 122 of the foot 120 has a much greater area than the light emitting surface 124 of the optical fiber 114.

The photo-therapy handpiece 112 has an optical fiber drive assembly 126. The second preferred embodiment may include a mechanical limiter 128. A catch mechanism 130 has a first position, as illustrated in FIG. 4, to hold the optical fiber drive assembly 126 in a "loaded" position. The catch mechanism 130 is movably attached to the handpiece body 118 such that it has a second position, as illustrated in FIG. 5, in which it leaves the motion of the optical fiber 114 unimpeded.

In the second preferred embodiment, the optical fiber drive assembly 126 has an optical fiber attachment portion 134 disposed in the interior region of the handpiece body 118. Preferably, the optical fiber attachment portion 134 is a flange which is bonded to the optical fiber 114. The optical fiber drive assembly 126 has a driving component 136 which is preferably a spring, although other drive components can be employed as described above. The spring is preferably in contact with the optical fiber attachment portion 134 at one end, and in contact with the handpiece body 118 at an opposing end. Preferably, a pair of damping components 138 are in contact with the optical fiber attachment portion 134 at one end, and are in contact with the handpiece body 118 at an opposing end 140. In this embodiment, damping components 138 are hydraulic cylinders although other damping components may be employed as described above.

The top surface 129 of the damping component 138 provides a mechanical limiter 128 in one preferred embodiment. In another preferred embodiment of the limiter 129 the damping component 138 has a piston 129 which is stopped by the opposing end 140 of the damping component 138.

The catch mechanism 130 is preferably pivotally attached at a point 142. The handpiece body 118 defines orifices 148 and 150 to permit the optical fiber 114 to pass therethrough. The optical fiber 114 has a radio-opaque marker 152 at the distal end 116 of the optical fiber 114 in a preferred embodiment. Gold and iridium are suitable materials for radio-opaque marker 152.

The operation of the trans-myocardial laser revascularization device 100 according to the second preferred embodiment of the invention is very similar to the operation of the device according to the first embodiment. However, in the second preferred embodiment, the optical fiber 114 enters the handpiece body 118 at the orifice 150 and protrudes through the center of the foot 120. Fiducial markers 154 can be placed on the fiber at the orifice 150, or at other suitable location, to provide visual assurance that fiber motion is attained when the catch mechanism 130 is released. Similar markings can be used with the first embodiment also.

Although the specification describes the trans-myocardial laser revascularization device and method, and the phototherapy handpiece in detail according to the preferred embodiments, those who are skilled in the art will readily appreciate that many modifications of the preferred embodiments are possible without departing from the novel teachings and advantages of this invention. One such modification would apply the device to excimer laser angioplasty. All such modifications are intended to be included within the scope of this invention as defined in the following claims.

We claim:

1. A phototherapy handpiece, comprising:
    a handpiece body that defines an interior region and has an outer surface; and
    an optical fiber drive assembly disposed at least partially within said interior region of said handpiece body having a first end fixed to said handpiece body and a second end having an optical fiber attachment portion that is movable relative to said handpiece body;
    wherein said optical fiber drive assembly includes:
        a driving component which causes said optical fiber attachment portion to move relative to said handpiece body, and
        a damping component which resists a motion of said optical fiber attachment portion such that said optical fiber attachment portion attains a substantially constant speed motion relative to said handpiece body.

2. A phototherapy handpiece according to claim 1, wherein said driving component is a spring.

3. A phototherapy handpiece according to claim 2, wherein said damping component is a hydraulic cylinder.

4. A phototherapy handpiece according to claim 1, further comprising a mechanical limiter adjustably attached to said handpiece body cooperating with said drive assembly to limit said motion of said optical fiber attachment portion.

5. A phototherapy handpiece according to claim 4, wherein said handpiece body has fiducial marks to indicate an extent of progress of said optical fiber attachment portion during said motion of said optical fiber attachment portion.

6. A phototherapy handpiece according to claim 1, further comprising:
a catch mechanism moveably attached to said handpiece body,
wherein said catch mechanism has:
a first position in which said optical fiber attachment portion is held at a substantially fixed position relative to said handpiece body, and
a second position in which said optical fiber attachment portion is released from said fixed position.

7. A phototherapy handpiece according to claim 6, wherein said catch mechanism operates in coincidence with a phototherapy light source such that said phototherapy light source is off while said catch mechanism is in said first position, and said phototherapy light source is on while said catch mechanism is in said second position.

8. A phototherapy handpiece according to claim 7, further comprising a mechanical limiter adjustably attached to said handpiece body, cooperating with said drive assembly to limit said motion of said optical fiber attachment portion.

9. A phototherapy device, comprising:
a handpiece;
an optical fiber having a distal end and a proximal end, said optical fiber being attached to said handpiece; and
a phototherapy light source disposed at said proximal end of said optical fiber, said phototherapy light source being arranged to input light into said optical fiber,
wherein said handpiece includes:
a handpiece body that defines an interior region and has an outer surface, and
an optical fiber drive assembly disposed at least partially within said interior region of said handpiece body having a first end fixed to said handpiece body and a second end having an optical fiber attachment portion that is movable relative to said handpiece body;
wherein said optical fiber drive assembly includes:
a driving component which causes said optical fiber attachment portion to move relative to said handpiece body, and
a damping component which resists a motion of said optical fiber attachment portion such that said optical fiber attachment portion attains a substantially constant speed motion relative to said handpiece body.

10. A phototherapy device according to claim 9, wherein said handpiece body outer surface defines a foot, said foot of said handpiece having a surface area that is much greater than a surface area of a light emitting surface of said optical fiber.

11. A phototherapy device according to claim 9, wherein said optical fiber has a radio-opaque marker at said distal end of said optical fiber, said radio-opaque marker being visible under fluoroscopy.

12. A phototherapy device according to claim 9, wherein a portion of said optical fiber drive assembly including said optical fiber attachment portion is external to said handpiece body, and
said optical fiber is attached to said optical fiber attachment portion such that said optical fiber is external to said handpiece body.

13. A phototherapy device according to claim 9, wherein said optical fiber attachment portion is disposed in said interior region of said handpiece body such that said optical fiber is attached to said optical fiber attachment portion in said interior region defined by said handpiece body, and said handpiece body defines a plurality of orifices which permit said optical fiber to pass therethrough.

14. A phototherapy device according to claim 9, wherein said optical fiber includes a plurality of single optical fibers.

15. A phototherapy device according to claim 9, wherein said phototherapy light source is a laser.

16. A phototherapy method comprising:
performing mechanical work on a phototherapy handpiece, wherein said mechanical work is stored in the form of potential energy by an optical fiber drive assembly disposed at least partially within an interior region of said phototherapy handpiece;
placing said phototherapy handpiece in contact with a treatment area of a patient's body; and
releasing said optical fiber drive assembly thus permitting said potential energy to be converted into kinetic energy which includes kinetic energy of motion of said optical fiber relative to said phototherapy handpiece,
wherein at about the same time of said releasing of said optical fiber drive assembly, said method includes turning a laser phototherapy light source on such that said laser phototherapy light source is on while said optical fiber moves relative to said phototherapy handpiece.

17. A phototherapy method, comprising:
performing mechanical work on a phototherapy handpiece, wherein said mechanical work is stored in the form of potential energy by an optical fiber drive assembly disposed at least partially within an interior region of said phototherapy handpiece;
placing said phototherapy handpiece in contact with a treatment area of a patient's body; and
releasing said optical fiber drive assembly, thus permitting said potential energy to be converted into kinetic energy which includes kinetic energy of motion of said optical fiber relative to said phototherapy handpiece,
wherein after said releasing, said phototherapy method includes damping motion of said optical fiber so that said optical fiber moves at a substantially constant speed.

18. A phototherapy method according to claim 16, wherein said releasing of said optical fiber drive assembly comprises releasing a catch mechanism on said optical fiber drive assembly.

19. A phototherapy method according to claim 17, wherein at about the same time of said releasing of said optical fiber drive assembly, said method includes turning a laser phototherapy light source on such that said laser phototherapy light source is on while said optical fiber moves relative to said phototherapy handpiece.

20. A phototherapy method, comprising:
performing mechanical work on a phototherapy handpiece, wherein said mechanical work is stored in the form of potential energy by an optical fiber drive assembly disposed at least partially within an interior region of said phototherapy handpiece;
placing said phototherapy handpiece in contact with a treatment area of a patient's body;

releasing said optical fiber drive assembly, thus permitting said potential energy to be converted into kinetic energy which includes kinetic energy of motion of said optical fiber relative to said phototherapy handpiece; and adjusting a mechanical limiter which is adjustably attached to said phototherapy handpiece, said mechanical limiter providing a mechanical limiter end at a desired position to stop a progression of said optical fiber in a distal direction, wherein said adjusting of said mechanical limiter is performed prior to said releasing of said optical fiber drive assembly.

* * * * *